(12) United States Patent
Columbus

(10) Patent No.: US 7,604,777 B2
(45) Date of Patent: Oct. 20, 2009

(54) CARTRIDGE FOR CONTAINING A SPECIMEN SAMPLE FOR OPTICAL ANALYSIS

(75) Inventor: Richard L. Columbus, Rochester, NY (US)

(73) Assignee: Veridex, LLC, Raritan, NJ (US)

( * ) Notice: Subject to any disclaimer, the term of this patent is extended or adjusted under 35 U.S.C. 154(b) by 832 days.

(21) Appl. No.: 10/988,057

(22) Filed: Nov. 12, 2004

(65) Prior Publication Data
US 2005/0063863 A1    Mar. 24, 2005

Related U.S. Application Data

(62) Division of application No. 10/074,900, filed on Feb. 12, 2002, now Pat. No. 6,861,259.

(60) Provisional application No. 60/268,101, filed on Feb. 12, 2001.

(51) Int. Cl.
*G01N 33/48* (2006.01)

(52) U.S. Cl. .................. 422/102; 422/101; 422/82.05; 356/246; 435/268.7; 435/304.3; 435/305.1; 435/305.4

(58) Field of Classification Search .............. 422/82.05, 422/101, 102; 356/246; 435/288.7, 304.3, 435/305.1, 305.4
See application file for complete search history.

(56) References Cited

U.S. PATENT DOCUMENTS

| | | |
|---|---|---|
| 3,124,281 A | 3/1964 | Stull |
| 3,276,640 A | 10/1966 | Kessler |
| 4,427,138 A | 1/1984 | Heinlein |
| 4,569,464 A | 2/1986 | Wassilieff |
| 4,849,173 A | 7/1989 | Chang |
| 4,859,610 A | 8/1989 | Maggio |
| 4,933,291 A | 6/1990 | Daiss |
| 5,026,526 A | 6/1991 | Quenin |
| 5,089,417 A | 2/1992 | Wogoman |
| 5,149,506 A | 9/1992 | Skiba |
| 5,179,862 A | 1/1993 | Lynnworth |
| 5,211,313 A | 5/1993 | Lucking |
| 5,246,669 A | 9/1993 | Hayashi |
| 5,277,873 A | 1/1994 | Hsei |
| 5,302,348 A | 4/1994 | Cusack |
| 5,578,269 A | 11/1996 | Yaremko |
| 5,658,801 A | 8/1997 | Poissant |
| 5,714,123 A | 2/1998 | Sohrab |
| 5,772,966 A | 6/1998 | Maracas |
| 5,780,304 A | 7/1998 | Matzinger |
| 5,795,543 A | 8/1998 | Poto |
| 5,799,829 A | 9/1998 | Lier |
| 5,800,781 A | 9/1998 | Gavin |
| 5,814,275 A | 9/1998 | Lewis |
| 5,814,277 A | 9/1998 | Bell |
| 5,882,942 A | 3/1999 | Kagaya |
| 5,958,349 A | 9/1999 | Peterson |

(Continued)

*Primary Examiner*—Lyle A Alexander

(57) ABSTRACT

A cartridge for holding a test specimen with an extremely small volume. The cartridge has a test chamber and a vestibule through which the test fluids are inserted into the test chamber. The cartridge has a stopper having a pair of seals, the first of which seals the test chamber inlet between the vestibule and the test chamber, and the second, of which seals the mouth of the vestibule so that when the stepper is in place, the test chamber is closed to the admission of air or other contaminants and the vestibule is similarly closed against escape of the overflow from the test chamber.

4 Claims, 4 Drawing Sheets

U.S. PATENT DOCUMENTS

| | | |
|---|---|---|
| 5,985,153 A | 11/1999 | Dolan |
| 6,013,188 A | 1/2000 | Terstappen |
| 6,013,532 A | 1/2000 | Liberti |
| 6,184,040 B1 | 2/2001 | Polizzotto |
| 6,239,445 B1 | 5/2001 | Shaeef |
| 6,271,046 B1 | 8/2001 | Chandler |
| 6,342,183 B1 | 1/2002 | Lappe |
| 7,011,794 B2 * | 3/2006 | Kagan et al. ................. 422/102 |
| 2001/0053336 A1 | 12/2001 | Hammer |

* cited by examiner

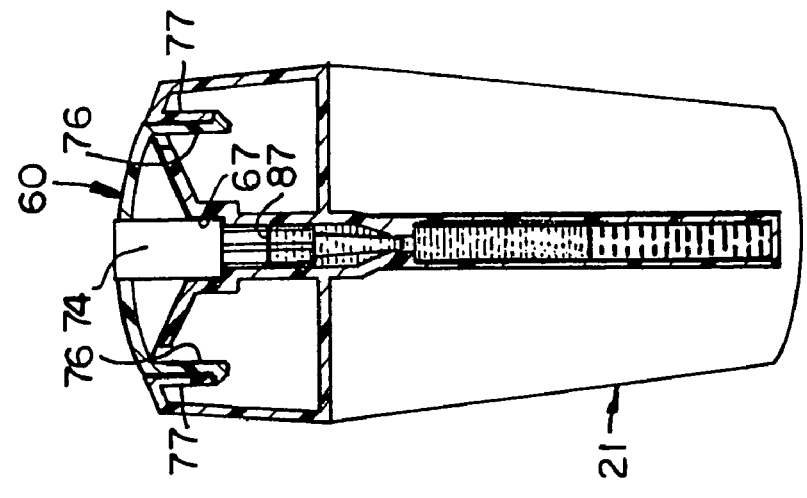
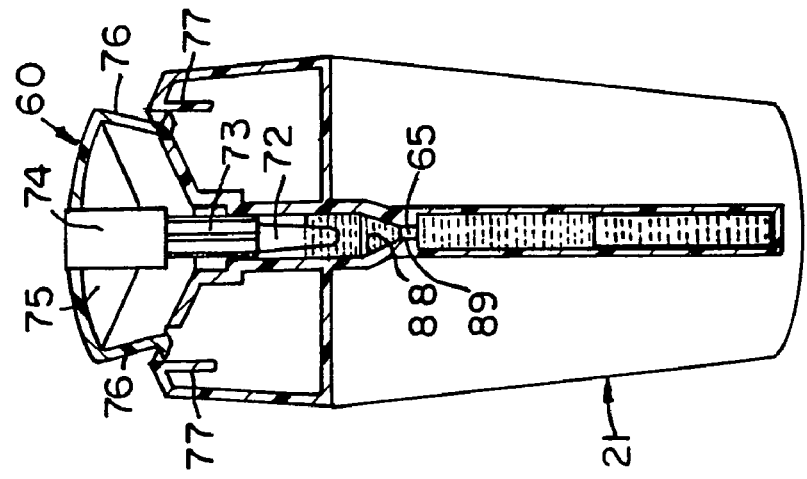
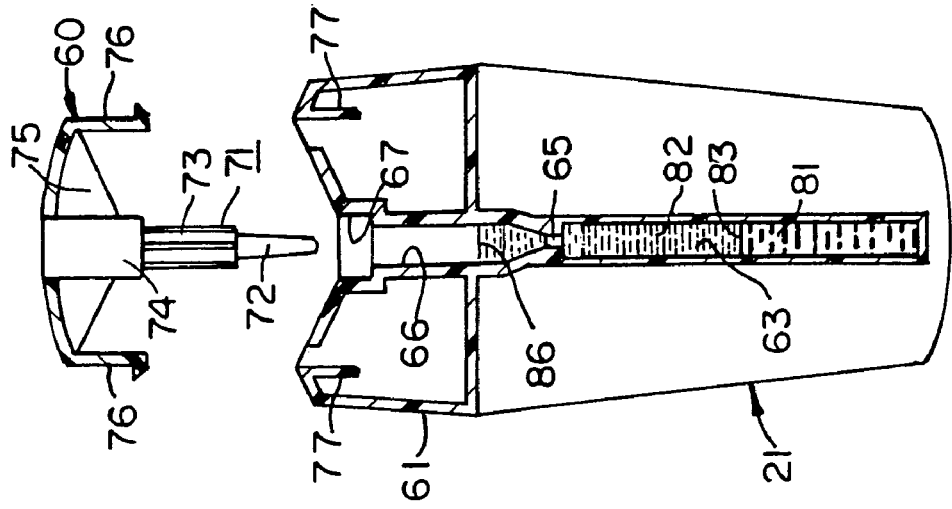

CARTRIDGE FOR CONTAINING A SPECIMEN SAMPLE FOR OPTICAL ANALYSIS

CROSS-REFERENCE TO RELATED APPLICATIONS

This is a divisional of Ser. No. 10/074,900, filed on Feb. 12, 2002 now U.S. Pat. No. 6,861,259 which claims the benefit of U.S. Provisional Application No. 60/268,101, filed Feb. 12, 2001 incorporated in full by reference herein.

FIELD OF THE INVENTION

The present invention relates to a cartridge having a chamber for containing a specimen sample for optical analysis and has particular application to a cartridge enabling analysis of a small sample of a biological specimen without the loss of any sample. The invention is particularly adapted to analyze blood, using a microscope or another suitable detector which positions the specimen within a magnetic field for magnetic separation of target components within the specimen.

BACKGROUND OF THE INVENTION

When performing optical analysis on specimens, it is customary to discard the specimen after the optical analysis. For rare cells, however, it is often desirable to preserve the specimen for further testing or for use in further procedures. In certain procedures, it is desirable to select a specimen from a relatively small sample, in the order of 10-100 ml, and it is likely that the volume of the specimen which may be extracted from such a small sample is limited, making it especially important to avoid destruction of the specimen or any substantial part thereof. It is likewise important to avoid contamination of the specimen and to avoid conditions which would lead to deterioration of the specimen or impairment of the analysis.

One cause of specimen deterioration is exposure of the specimen to air bubbles which may not only cause deterioration of the specimen but the presence of bubbles may adversely affect the optical analysis of the specimen.

Numerous devices are available for containing a specimen for analysis, but there has been no collection chamber which is designed to isolate a small sample for analysis and to preserve the sample for additional testing Specifically, there has been no collection device which enables the exclusion of air in the form of bubbles or in other forms from the sample chamber.

For example, U.S. Pat. No. 5,246,669 discloses a sampling device for collecting a small sample and mixing it with a test liquid. In this patent, the device provides a pickup device which extracts a small sample from a larger quantity of solid or semi-solid material to be tested. The device separates the small sample from the residue and isolates the residue so as to avoid contamination of the small sample or the surrounding atmosphere. The device does not provide for salvaging either of the test sample or the residue and does not have any provision for excluding air in the form of bubbles from the test liquid.

SUMMARY OF THE INVENTION

The present invention provides a novel cartridge for use in optical analysis of specimens having a test chamber which contains the specimen for subsequent procedures which, enables optical analysis of the specimen without less of any substantial part thereof and which enables the specimen to be retained in the cartridge test chamber in the absence of air bubbles or other contaminants. The invention also provides a novel method for handling specimens which enables the specimen to be presented in a test chamber for optical analysis without the risk of loss of any substantial part of the specimen and without the risk of inclusion of air bubbles or exposure to other deteriorating conditions in the test chamber.

More specifically, the present invention provides a cartridge which may be mounted in a microscope or other optical detection equipment which positions target cells of the sample in the field of observation of the equipment in an orderly array.

The specimen sample is introduced into a test chamber within the cartridge along with a buffer solution in which the respective properties of the specimen and the buffer solution are such as to provide an interface separating the buffer solution from the sample. The sample chamber is elongated with a port at one end. Preferably, the buffer solution is of a density less than or equal to the density of the sample so that when the chamber is disposed with the ported end upright, the buffer solution is positioned above the interface and the sample is positioned below the interface. During the filling of the chamber, any air or other contaminants which are less dense than the buffer solution are allowed to gravitate upwardly through the buffer solution towards the port in the upper end of the chamber. The chamber is designed with a vestibule which provides an overflow reservoir which may be seated both from the test chamber and the exterior environment. A stopper is provided for sealing both ends of the vestibule and has a probe which extends into the buffer solution above the interface. As the stopper is engaged with the port of the test chamber, the probe displaces the buffer into the vestibule. The stopper has a primary seal which closes the test sample chamber from the vestibule and a second seal which closes the outside entrance of the vestibule to prevent escape of the buffer from the vestibule. The vestibule thus serves as an overflow receptacle. The first seal closes the test chamber after any deleterious air bubbles in the chamber have migrated into the vestibule. Thereafter, the second seal closes the overflow chamber to retain the buffer solution against loss. When in place, the stopper permits the cartridge to be manipulated into position in the optical detecting device in an orientation which positions the test chamber so that the target cells are in a suitable array within the field of detection of the detection equipment,

BRIEF DESCRIPTION OF THE DRAWINGS

All of the objects of the invention are more fully set forth hereinafter with reference to the accompanying drawings, wherein:

FIGS. 5A, 5B and 5C are sectional views of the cartridge in loading position illustrating the cooperation between the cartridge body and the stopper to entrap the specimen in the cartridge in the absence of air, FIG. 5A showing the stopper removed with the specimen and the buffer in place within the chamber and the vestibule; FIG. 5B is view similar to FIG. 5A showing the penetration of the probe of the stopper into the buffer within the vestibule; and FIG. 5 showing the stopper in place closing both the port between the chamber and the vestibule and the upper end of the vestibule;

DESCRIPTION OF THE PREFERRED EMBODIMENTS

The cartridge of the present invention is particularly adapted for use in a detecting apparatus such as shown in U.S. Pat. No. 6,013,532, which issued to Liberti et al. on Jan. 11, 2000, and described in a paper entitled "Optical Tracking and Detection of Immunomagnetically Selected and aligned Cells" by Arian G. J. Tibbe et al, published by *Nature Biotechnology*, Vol. 17, December 1999, pp 1210-1213, both of which are incorporated by reference herein. The apparatus, shown schematically in FIG. 1 of the patent, is effective to immobilize target entities, such as cells, within a fluid medium for observation, analysis or manipulation. The target entities are magnetically labeled and deposited in a test chamber where they are manipulated by a magnetic field to dispose the target entities in a mono-layer along a wall of the test chamber. A discussion of automated magnetic separation techniques is included in U.S. Pat. No. 5,985,153 which issued to Gerald J. Dolan et el. on Nov. 16, 1999, and in a paper entitled "Cell Analysis System Based on Immunomagnetic Cell Selection and Alignment Followed By Immunofluorescent Analysis Using Compact Disk Technologies" by Arian G. J. Tibbe et el., published in *Cytometry*, 43:31-37 (2001), both of which are also incorporated herein by reference.

Figure 1:
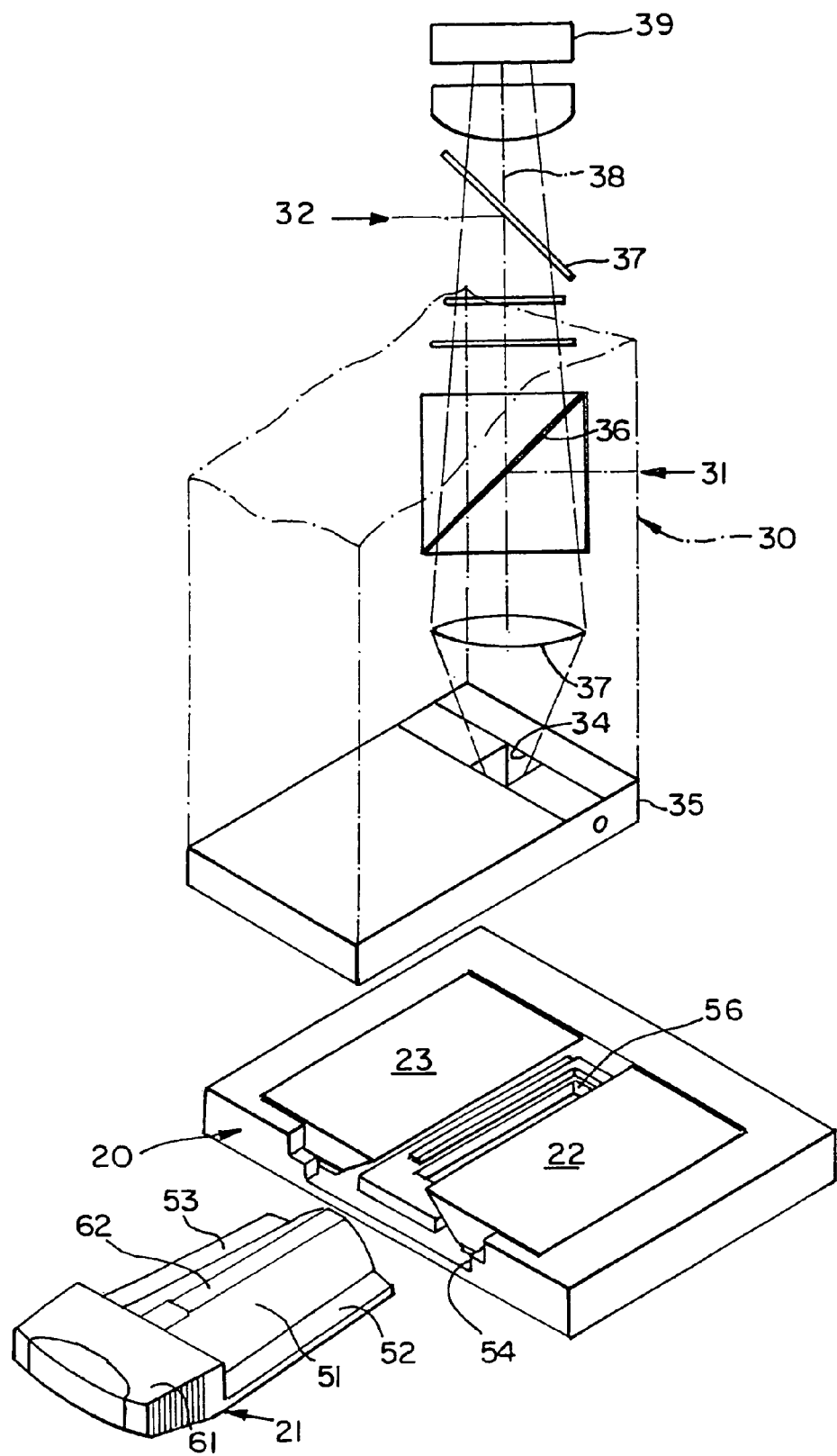
FIG. 1 is a schematic representation of a detecting apparatus for analyzing a test liquid in a cartridge made in accordance with the present invention.
Figure 2:
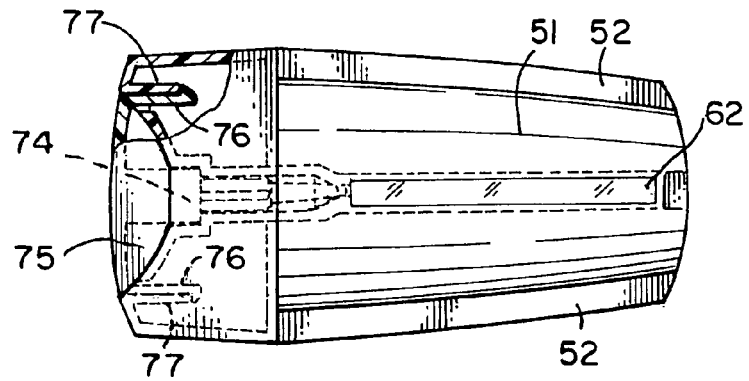
FIG. 2 is a front view of a cartridge embodying the present invention with its stopper in place and with a portion broken away to illustrate the interengagement of the stopper with the body of the cartridge.
Figure 3:
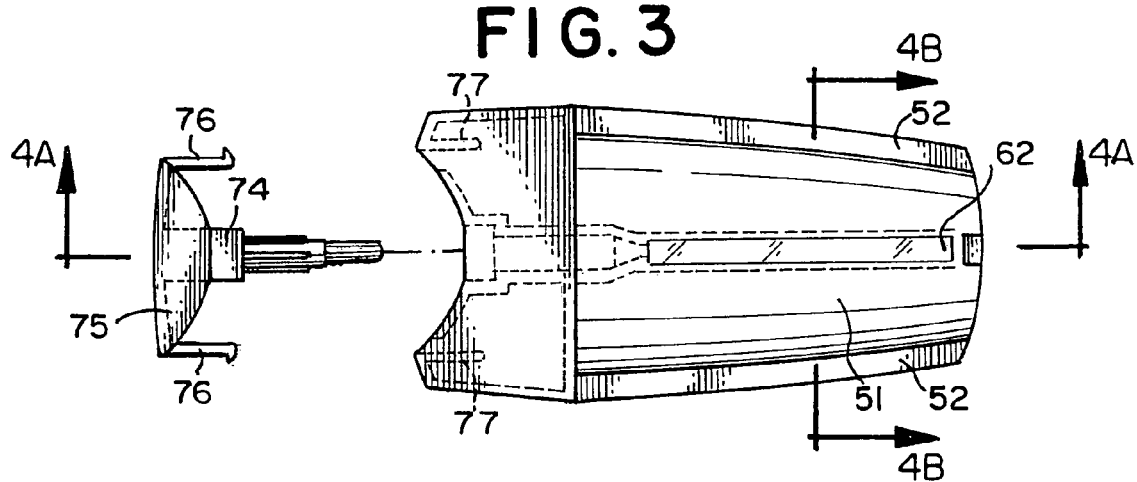
FIG. 3 is a view similar to FIG. 2 showing the stopper removed from the body of the cartridge.
Figure 4A:
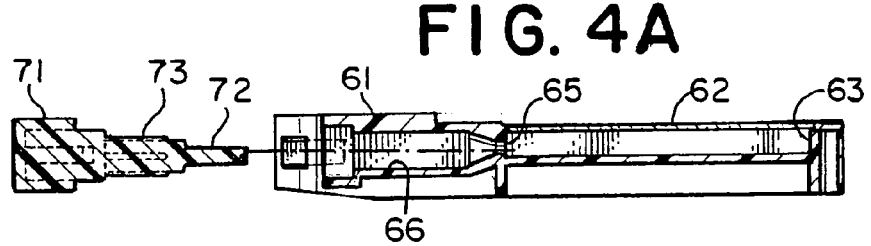
FIGS. 4A and 4B are sectional views taken on the lines 4A-4A and 4B-4B of FIG. 3, respectively.
Figure 4B:
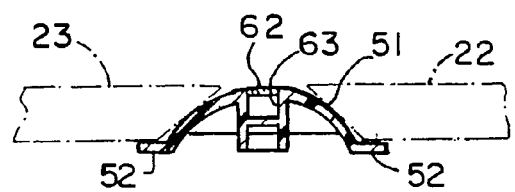

Referring to FIG. 1, a cartridge embodying the invention is shown at 21 mounted in a receptacle 20 having a pair of opposed magnetic poles 22 and 23 which have a gap formed therebetween. In the illustrated detecting apparatus, the receptacle 20 is positioned horizontally in the path of the optical system of the apparatus with the gap upwardly, but for other applications the receptacle may be positioned vertically. In FIG. 1, the lower surfaces of the poles 22 and 23 are tapered toward the gap so that magnetic field applied to the chamber is non-uniform and has a substantially vertical gradient effect directed toward the gap transverse to the longitudinal axis of the cartridge 21 to urge magnetically-responsive particles within the chamber towards the wall of the cartridge which is substantially co-planar with the gap. The target entities are collected in an orderly monolayer on the interior surface of the test chamber, and an automated observation system can be configured to provide relative motion between the cartridge and the light-gathering elements of the observation system in order to track the collected target entities for automated enumeration, which can include spectral analysis of light emitted, absorbed or scattered by the collected targets.

The system shown schematically in FIG. 1 comprises optical tracking beam analysis components 30 similar to those employed for reading compact discs known in the audio and data storage arts. Briefly, a pair of laser diodes generate parallel beams of light 31 and 32. One beam is employed by the analysis system for locating and tracking lines of the target entities. The other beam is used for detecting the presence of collected target entities adjacent to a located line. Relative motion between the cartridge 21 and the optical elements of the analysis system is provided by a mechanical translation unit 35 which has an aperture 34. Coordination of the functions of the analysis system is provided by a microprocessor (not shown). The tracking beam 31 which is reflected by dichroic mirror 36 through the aperture 34 is focused upon the upper surface of the cartridge 21 by an objective lens 37. The detecting beam 32 is reflected by the dichroic mirror 37 through the dichroic lens 36 and the objective lens 37.

Light reflected by the tracking lines and the target entities will be transmitted through dichroic mirrors 36 and 37 toward a photo detector 39 as indicated at 38. The detector 39 generates a data signal which is fed to the microprocessor for the unit 35, as described more fully in the above-mentioned U.S. Pat. No. 5,985,153 to control the translation of the unit 35 and process the data provided by the detector 39.

The cartridge 21 may also be used in other detecting apparatus such as a microscope, as described in the above-mentioned U.S. Pat. No. 6,018,532 in which the stage is designed to receive the receptacles 20 so as to position the surface of the cartridge in the light path of the microscope. As noted above, the orientation of the test chamber may be horizontal, vertical or at any angle determined by the instrumentation of the detecting apparatus.

When in the orientation shown in FIG. 1, the cartridge 21 has a domed body portion 51 having outwardly projecting glides 52 and 53 on opposite sides thereof. The glides 52 and 53 are designed to slide into guideways 54 and 55 in the receptacle so that the domed body portion of the cartridge underlies the lower surfaces of the poles 22 and 23. Intermediate the guideways 54 and 55, the receptacle has a slot 56 providing an optical path through the bottom of the receptacle. The optical path registers with the longitudinal centerline of the cartridge when the cartridge is inserted into position within the receptacle 20. The cartridge has a handle portion 61 for enabling the insertion and removal of the cartridge into and from the receptacle. The cartridge is formed of a nonmagnetic inert material, such as polycarbonate, polystyrene or acrylic with fluorescent additives and is formed to provide a rigid chamber which may be manipulated into and out of the optical path of the optical analysis system. The cartridge has a flat land surface 62 at the top of the dome 51 and the body of the receptacle provides a test chamber 63 underlying the land surface 62. When positioned in the receptacle 20, the test chamber 63 is aligned with the aperture 56 of the receptacle along the light path of the detecting apparatus in which the receptacle 20 is mounted, and to this end, the land surface 62 is optically clear to provide an analytic viewing surface.

In the present instance, the test chamber 63 is closed at the distal end remote from the handle 61 and has an inlet opening 65 at the proximal end adjacent the handle 61. The inlet 65 is positioned in the center of the end wall of the test chamber 63 at the proximal end so that when the cartridge is disposed vertically for filling, the inlet opening 65 is at the uppermost part of the chamber 63. The body of the cartridge provides a vestibule chamber 66 having an enlarged mouth 67 at its entrance end. The vestibule chamber 66 communicates with the test chamber 63 through the inlet opening 65. Between the mouth 67 and the inlet 65, the vestibule 66 provides an overflow reservoir, as described more fully hereinafter. The test chamber 63 is adapted to be closed by a plunger 71 having a probe 72 adapted to sealingly engage in the inlet 65 of the test chamber 63. Rearwardly of the probe 72, the stopper has a ribbed stem 73. 73 terminating in a plug 74 which is adapted to sealingly engage in the mouth 67 when the stopper is fully inserted through the vestibule 66. When fully inserted, the plug 74 closes the proximal end of the vestibule 66. Beyond the plug 74, the stopper has a handhold 75 and inwardly projecting clips 76,76 which engage behind keeper elements 77,77 in the handle 61 of the cartridge.

The projecting part of the stopper including the probe 72 and the plug 74 comprise an elastomeric material such as a thermoplastic elastomer (DYNAFLEX®), or other elastomeric material capable of forming seals with the inlet 65 and the mouth 67, respectively. Preferably, the durometer of the elastomeric material is in the range of 60-90. The handhold 75 of the stopper and the clips 76 is formed of a semi-rigid resilient plastic material, such as polycarbonate, polystyrene or acrylic, so that twisting the handhold about the axis of the stopper flexes the clips 76,76 to release their engagement with the keepers 77,77, The handhold 75 of the plunger 60 is nested within the handle 62, and is releasably retained in nested position by the clips 76 latching behind the keepers 77, as shown in FIG. 5C. For ease of operation, the illustrated resilient-overflow-ear closure of the handle may be replaced with other closures, such as a screw-cap closure.

As shown in FIGS. 1-4A, when in the illustrated optical analysis system, the cartridge is disposed with its longitudinal axis horizontal so that the flat land area 62 of the test chamber 63 is disposed within the field of observation of the detection equipment. When filling the test chamber 63, the cartridge is disposed with its longitudinal axis upright with the vestibule 66 disposed above the test chamber 63. As shown in FIGS. 5A-5C, a test liquid 81 is introduced into the test chamber 63 along with a buffer solution 82. The buffer solution has a density which is less than or equal to the test liquid so that there is a liquid interface provided between the two solutions at 83. The volume of the buffer solution is sufficient to completely fill the test chamber 63. The filling operation excludes air from the test chamber 63, and any air bubbles remaining in the buffer solution will gravitate upwardly through the inlet 65 into the vestibule 66. On one side, the upper side of the interface 83, the buffer solution fills the chamber 63 and on the other side, the lower side of the interface 83, the test solution extends to the closed bottom of the test chamber. As shown in FIG. 5A, the buffer solution inserted in the test chamber has a surface level 86, in the present instance within the vestibule 66 adjacent the inlet 65.

The construction and arrangement of the chamber insures that air bubbles are excluded from the test chamber and pressure build-up in the unit is avoided. As shown in FIGS. 5A-C, when the stepper 60 is inserted into the vestibule 66, the probe 72 displaces the buffer solution and causes the surface of the buffer solution to rise within the vestibule until the probe 72 contacts the inlet 65. As shown, the inlet 65 has a flared mouth 88 and a cylindrical channel 89 below the flared mouth. At this point, the surface of the buffer solution is shifted upwardly to an elevated fill line 87 (FIG. 5C). Further movement of the stopper downwardly causes the tip of the probe 72 to enter the channel 89 of the inlet 65. When the probe 72 engages the cylindrical channel 89, the probe effects a first seal, closing communication between the test chamber 63 and the vestibule 66. Further penetration of the probe 72 into the cylindrical portion of the cylindrical channel 89 of the inlet 65 perfects the seal. Because the tip of the probe 72 closes the cylindrical channel 89, and, in the present instance, the internal diameter of the channel 89 of the inlet 65 is less than the internal dimensions of the chamber 63 so that the volume of buffer solution in the channel is minimal, and the engagement of the probe 72 into the channel 89 when effecting the first seal does not significantly increase the pressure within the test chamber 63. The vestibule remains open at the top until the plug 74 enters the mouth 67, a/lowing the vestibule to remain at ambient pressure.

The design of the present invention may be used for any analysis chamber, but it has been specifically created for analysis chambers for testing extremely small samples having a volume of less than 1 ml. In the illustrated embodiment, referring to FIG. 4B, the width of the chamber 63 below the land area 62 is approximately 8 mm and the height is approximately 4 mm, providing a cross-sectional area in the range of 10 to 14 square millimeters. The length is approximately 80 mm. The volume of the chamber 63 should be in the range between 22 µl and 675 µl, preferably at least 815 µl. The diameter of the inlet 65 is in the range between 0.0881 mm and 3.18 mm, and preferably is 2.85 mm, providing a flow area of approximately 10 square millimeters. Beyond the inlet 65, the vestibule flares out, in this case to a diameter of 4.23 mm, and extends approximately 14 mm to the mouth 67 which, in this case, has a width of 6.8 mm. With the plug fully inserted, the volume of the vestibule 66 is preferably at least 95 µl. The width of the test chamber at the upper wall is slightly more than the diameter of the channel 89 of the inlet 65. Although not shown in the figures, the corners around the perimeter of the upper wall are broken or beveled, so as to avoid entrapment of any air bubbles gravitating upwardly through the chamber 63. The bevel is preferably at an angle of between 2° and 30" relative to the longitudinal axis of the chamber 63 and the inlet 65.

Figure 6:
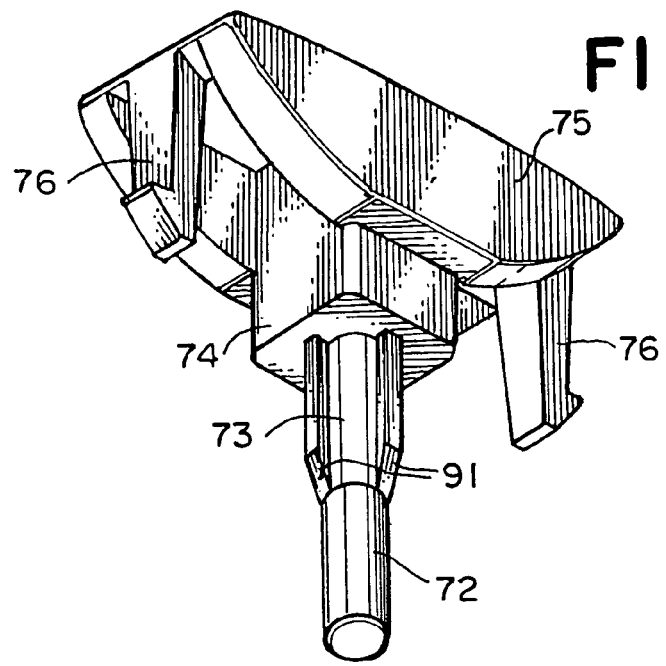
FIG. 6 is a perspective view of the stopper shown in FIGS. 2-5.
Figure 7:
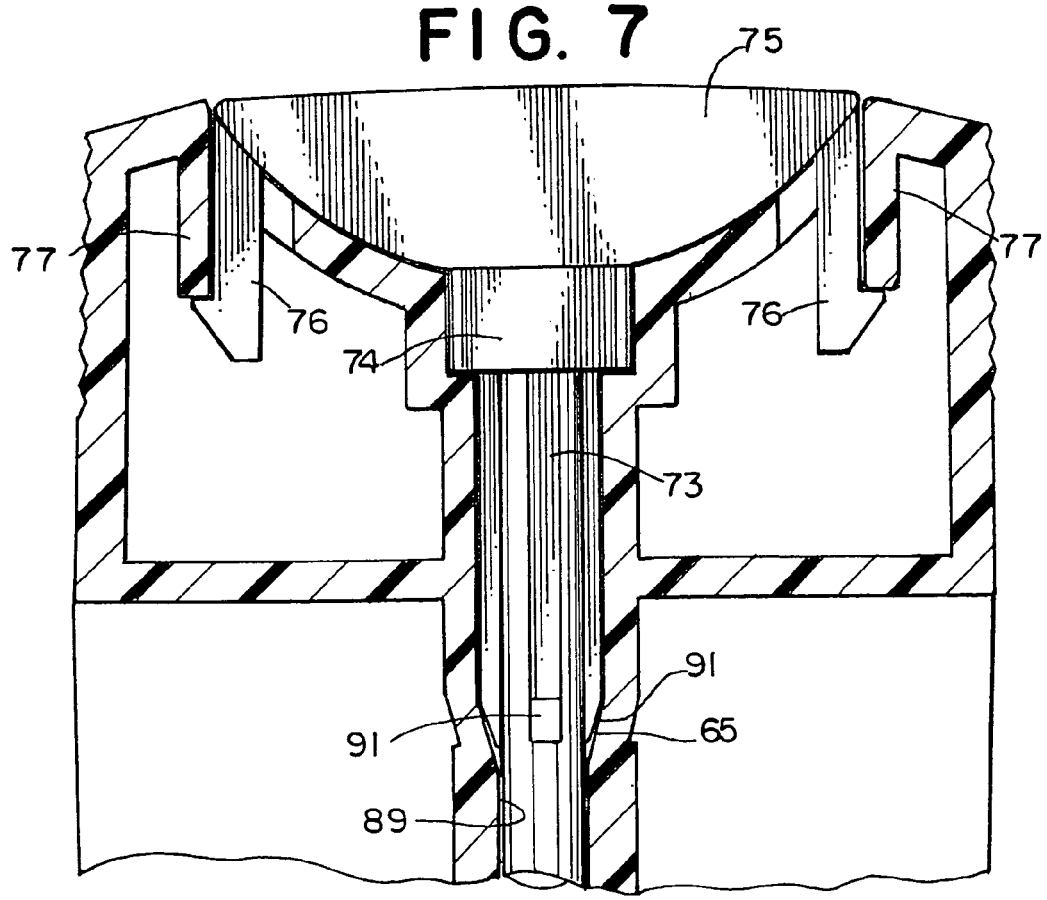
FIG. 7 is an enlarged fragmentary sectional view of the cartridge with the stopper operatively engaged with the body of the cartridge.

Further displacement of the stopper 60 allows the plug 74 at the proximal end of the stem 78 to engage in the mouth 67 of the vestibule and effect a second seal closing the upper end of the vestibule. As shown in FIGS. 6 and 7, the plug 74 is a rectangular block to mate with the mouth 67 which is in the form of a socket having a complementary rectangular form. The block 74 is of the same plastic material as the probe 72 having sufficient resiliency to effect a good seal with the socket 67 when engaged as shown in FIG. 5C. The displacement of the plug 74 in the socket 67 does not substantially increase the air pressure above the fill line 87.

The distance between the top of the cylindrical channel 89 of the inlet 65 and the bottom of the socket forming the mouth 67 is less than the distance between the tip of the probe 72 and the bottom of the plug 74 so that there is assurance that the probe enters into the channel 89 before the plug 74 seats against the bottom of the socket 67. This arrangement insures avoidance of any substantial pressure build-up in the vestibule 66. It is noted that the stem 73 has ribs 91 spaced circumferentially therearound so that the space between the ribs provides an adequate space to accommodate the buffer solution displaced during the penetration of the probe into the cylindrical portion 89 of the inlet. The resiliency of the plastic forming the stopper is sufficient to enable the clips 76 to be deflected out of engagement with the keeper element 77 for removal of the stepper 60 by simply twisting the handhold 75 about the longitudinal axis of the cartridge.

With the clips engaging the keeper element 77 to keep the stopper in place, air is confined within the vestibule 66 between the first and second seals, and the cartridge may be manipulated without fear of air bubbles or the like interfering with the optical analysis of the liquid in the test chamber 63. After being filled, the cartridge may be reoriented so that its longitudinal axis is horizontal for analysis in the detecting apparatus, as described above and illustrated in FIGS. 1-4, since the test chamber 63 is completely filled with liquid. It may be manipulated into other orientations, as may be required by the detecting apparatus chosen by the analyst. Any buffer solution 82 which is in contact with the test liquid 81 is retained within the cartridge, either in the test chamber 63 or within the vestibule 66, and there is little danger of loss of any significant part of the test liquid. The buffer solution which overlies the test liquid in the cartridge during the filling operation assures minimal exposure of the test liquid to air and that the risk of deterioration or contamination of the test liquid is diminished.

While a particular embodiment of the present invention has been herein illustrated and described, it is not intended to limit the invention to such disclosure, but changes and modifications may be made therein and thereto within the scope of the following claims.

The invention claimed is:

1. A cartridge containing a test chamber for use in apparatus for performing optical analysis of liquid specimens by optical observation, said apparatus having a receptacle for receiving the cartridge and positioning the test chamber of the cartridge in a field of observation of the apparatus to enable analysis of liquid within the test chamber, the apparatus having at least two magnetic poles positioned on opposite sides of the receptacle to apply a magnetic field to the cartridge, said cartridge comprising:

(a) a body of translucent plastic adapted to be slidably engaged in the receptacle of the apparatus between said magnetic poles to position the test chamber in the magnetic field of said poles, said body having a domed cross section with a flat area on the top of the dome extending along the longitudinal axis so as to be positioned in the field of observation of the apparatus, (b) a test chamber having an upper wall with a slightly larger diameter than an inlet channel wherein said upper wall contains beveled corners between 2° to 30° relative to the longitudinal axis of the chamber to avoid air bubble entrapment, and having a vestibule above said test chamber, said inlet between said test chamber and said vestibule, and a fill line located adjacent said inlet, said fill line determined by the surface of liquid inserted into said test chamber;

(c) a stopper having a first seal adapted to sealingly seat in the inlet and close the same, said stopper having a distal end adapted to enter the inlet of the test chamber below the fill line before the first seal closes said inlet, said distal end having a thickness sufficient to displace and excess volume of liquid upwardly through said inlet and position the surface of the liquid in said vestibule prior to said first seal closing said inlet, said first seal, upon being seated in the inlet, precluding air entrapment within the test chamber;

(d) said vestibule having a volume to form an overflow reservoir for receiving a volume of liquid that may be displaced upon seating the primary seal; and (e) a second seal remote form the first seal in said vestibule, said first and second seals defining therebetween the overflow reservoir, said second seal precluding migration of any overflow liquid past the second seal out of the system.

2. A cartridge according to claim 1 wherein said test chamber has a volume of at least 315 μl and said vestibule has a volume of at least 95 μl when the first of said stopper seals is seated in the inlet and the second seal is precluding migration of any overflow liquid past the second seal.

3. A cartridge according to claim 2 wherein said test chamber has a volume in the range of 22 μl to 675 μl.

4. A cartridge according to claim 1 wherein said test chamber has cross-sectional area in the range of 10 to 14 square millimeters and the inlet has a diameter of 2.35 mm.

* * * * *